US006780065B2

(12) United States Patent
Schwarz

(10) Patent No.: US 6,780,065 B2
(45) Date of Patent: Aug. 24, 2004

(54) DEVICE FOR ELECTRICAL CONNECTION OF A POWER LEAD TO AN ELECTRODE, IN PARTICULAR A MEDICAL SKIN ELECTRODE

(75) Inventor: Dieter Schwarz, Neubulach (DE)

(73) Assignee: Nicolay Verwaltungs-GmbH, Nagold (DE)

( * ) Notice: Subject to any disclaimer, the term of this patent is extended or adjusted under 35 U.S.C. 154(b) by 0 days.

(21) Appl. No.: 10/444,949

(22) Filed: May 27, 2003

(65) Prior Publication Data

US 2003/0228805 A1 Dec. 11, 2003

(30) Foreign Application Priority Data

Jun. 7, 2002 (DE) .......................................... 102 25 621

(51) Int. Cl.[7] ................................................ H01R 4/28
(52) U.S. Cl. ........................ 439/725; 439/310; 439/909
(58) Field of Search ................................ 439/310, 725, 439/909

(56) References Cited

U.S. PATENT DOCUMENTS

| 5,295,872 A | * | 3/1994 | Christensson | ................ | 439/822 |
| 5,454,739 A | * | 10/1995 | Strand | ......................... | 739/729 |
| 5,944,562 A | * | 8/1999 | Christensson | ................ | 439/729 |
| 6,357,089 B1 | * | 3/2002 | Koguchi et al. | .............. | 24/536 |
| 6,623,312 B2 | * | 9/2003 | Merry et al. | ................. | 439/729 |

FOREIGN PATENT DOCUMENTS

| DE | 3527916 | 2/1987 |
| DE | 3719474 | 12/1988 |
| DE | 19801173 | 7/1999 |
| DE | 19920481 | 1/2001 |

OTHER PUBLICATIONS

Office Action dated Jun. 17, 2002, German Priority Application No. 102 25 621.7 filed Jun. 7, 2002.

* cited by examiner

Primary Examiner—Michael C. Zarroli
(74) Attorney, Agent, or Firm—Roylance, Abrams, Berdo & Goodman, LLP

(57) ABSTRACT

A device for electrical connection of a power lead to an electrode, in particular a medical skin electrode, includes a first contact element for plugging onto the contact stud of a first electrode. The first contact element has a first energy-storage or spring element biasing a contact zone of the first contact element into engagement with the contact stud of the first electrode. A second contact element has two clamp jaws for clamping a second electrode. The second contact element can be actuated to open by an actuating element pivotal around an axis, against the action or bias of an energy storage.

54 Claims, 2 Drawing Sheets

DEVICE FOR ELECTRICAL CONNECTION OF A POWER LEAD TO AN ELECTRODE, IN PARTICULAR A MEDICAL SKIN ELECTRODE

BACKGROUND OF THE INVENTION

Devices for electrical connection of a power lead to an electrode, in particular a medical skin electrode, are disclosed in DE 37 19 474 A1. These connecting devices are used, for example, to measure physiological signals from living things, for example cardiac action voltages (electrocardiogram, EKG). For this purpose, electrodes are applied, for example, glued to the skin, and are connected to an electrical power lead via which the physiological signals in electrical form are routed to an evaluation unit. The device operates as a snap fastener and is snapped onto the contact stud of the electrode. The contact stud can be a separate part of an electrode of the conventional type or can, for example, with the bottom of a plate-shaped foot part, form the electrode surface itself.

Recently, a second type of electrode has been used, specifically so-called gel or film electrodes. These electrodes include a piece of metal foil or a piece of plastic film having an electrically conductive layer and coated with an electrically conductive gel. The detachable connection of one such electrode to a power lead in the form of a connecting cable can take place, or example, with an electrical clamp having two clamp jaws. At least one of the clamp jaws can swivel around the axis. The clamp jaws hold the essentially flat electrode, with which contact is to be made, between them by clamping. Similar clamps are known in other areas of engineering as "alligator clips".

DE 198 01 173 C1 discloses a device which can make electrical contact with a first contact element and electrodes having a contact stud, and can make contact with a second contact element with film electrodes. This device is characterized in that the clamp jaws of the second contact element can be actuated to open by means of an actuating slide extending transversely to the lengthwise direction of the clamp jaws. The first contact element is provided simply as an option, and has a through opening which is invariable in its clearance for the contact stud. The invariable clearance for the contact requires high actuating forces, and for some applications, does not satisfy the required contact reliability.

SUMMARY OF THE INVENTION

Objects of the present invention are to provide a generic device which overcomes the disadvantages of the prior art.

In particular, with the device, if necessary, both electrodes can make reliable contact with one terminal stud and film electrodes on a permanent basis, simultaneously and repeatedly. In one special embodiment of the present invention, the device is operable in an ergonomically favorable manner, is to have a compact construction, and is to be economical to manufacture.

These objects are obtained by a device for electrical connection of a power lead to an electrode, comprising a first contact element for receiving the contact stud of a first electrode. The first contact element has a first spring element for biasing a contact zone of the first contact element into contact stud with the first electrode. Also, the device has a second contact element having first and second clamping jaws for engaging a second electrode. The second contact element can be actuated to open by an actuating element which can be pivoted around the first axis, against the action of an energy storage, to an open position.

At the same time or alternatively, preferably electrodes of a first type or a second type make contact with the first and second contact elements, respectively. In particular, the first electrode can make contact with the first contact element. This electrode has a plug element, for example a contact stud.

In particular, film electrodes can make contact with the second contact element. The film electrode has a terminal lug which is flat.

The first contact element is preferably essentially flat. The opening actuation of the first contact element takes place preferably by deflecting or shifting the contact zones essentially parallel to the surface formed by the first contact element.

Of the two clamp jaws of the second contact element, the first clamp jaw can swivel or pivot, preferably around an axle fixed in the housing of the device. The second clamp jaw is formed in one piece, preferably as part of the base element of the housing. The opening actuation of the second contact element takes place by rotation or pivoting of the actuating element, preferably by an angle of less than 90°, for example roughly 45°. The rotation of the actuating element takes place against the action or bias of the first energy-storing or spring element of the first contact element and/or against the action of a second energy-storing or spring element of the second contact element. Alternatively or additionally, the actuation can take place against the action of a third energy-storing or spring element located between the actuating element and the housing element of the device.

In one special embodiment of the invention, when the rotary actuating element is actuated, the contact zone of the first contact element can be actuated to open. In particular, upon rotation, the first energy-storing or spring element deflects for energy storage. By the opening actuation of the contact zone of the first contact element, the contact stud can be inserted into the device almost without exerting any force. Upon subsequent resetting of the actuating element, the contact zone is brought into electrical contact with the contact stud of the electrode by the stored energy. Moreover, this contact-making of the first contact element mechanically saves the contact zones, and thus, ensures permanently reliable contact-making.

Preferably, the first contact element has two contact zones symmetrical relative to the insertion axis of the device onto the contact stud and essentially flat. Furthermore, the contact zones are preferably located on contact tongues, each being integral with a spring arm on its edge side facing the insertion opening for the contact stud and being movable in the radial direction relative to the insertion axis of the device for the contact stud into contact with the latter. The spring legs can be strip-shaped, can form the first energy-storing element, and are preferably angled relative to the surface of the contact tongues, especially bent at a right angle.

In one special embodiment of the present invention, the actuating element has a first actuator by which the first energy-storing element can be deflected when the actuating element turns. For example, the first actuator can be made as an actuating pin located eccentrically relative to the first axis on the actuating element that deflects the spring leg upon contact while turning.

In one special embodiment of the present invention, the actuation element has an axle journal pivotally supported in the guide element of the housing of the device. At least one section of the axle journal can have an eccentrically extending area on its outside peripheral surface. Upon rotation around the first axis, deflection of the first energy-storing element occurs in the radial direction relative to the first axis based on the contact between the first energy-storing element and the eccentrically extending area of the outside peripheral surface. The forces for actuating or deflecting the first energy-storing element are thus low and can be set, and, in particular, further reduced by the corresponding length of the lever of the actuating element.

In one special embodiment of the present invention, the actuating element has a second actuator. When the actuating element is rotated around the first axis, the first clamp jaw of the second contact element can be pivoted around a second axis against the action of an energy storage by the second actuator to actuate the second contact element to an open position. The energy storage exerts a reset force on the clamp jaws of the second contact element, and can fundamentally be formed by the first energy-storing element of the first contact element. Preferably, however, the resetting action is provided by a second energy-storing element formed by the second contact element, by directly engaging the second contact element, and/or by a third energy-storing element acting directly on the actuating element.

Preferably, the first axis of rotation for the actuating element and the second axis as the axis of rotation for the second contact element are oriented at a right angle. Furthermore, the second actuator includes a crank guide with a crank path having a radial component relative to the first axis. The length and/or the course of this crank path allows adjustment of the opening angle of the clamp jaws relative to the angle of rotation of the actuating element or adaptation to special applications. If the second actuator has a crank path and the first clamp jaw has a guide pin which fits into the crank path, simply replacing the actuator adapts the opening angle of the clamp jaws to the respective application chosen depending on the angle of rotation of the actuating element.

In one special embodiment of the present invention, the second contact element has a second energy-storing element for providing spring-loaded contact-making of one contact zone of the second contact element with the electrode with which contact is to be made. Preferably, the contact zones of the second contact element are formed unitarily in one piece as two legs which can be elastically deflected. Execution as a punched/bent part of a sheet metal is especially favorable with respect to production costs and contact reliability. Each of the two preferably flat legs is fixed on one of the two clamp jaws, respectively. The U-shaped connecting section connects the two legs to be elastically deflected and can at the same time form a stop for the insertion of the electrode with which contact is to be made into the clamp mouth formed by the clamp jaws.

In one special embodiment of the present invention, the first and second contact elements are made in one piece. In any case, the two contact elements are connected to one another in an electrically conductive manner. The connection can be made for example by welding, especially spot welding, soldering, especially brazing, cementing, riveting, screwing or the like. The two contact elements are arranged in succession in the housing of the device such that they can be used alternately or simultaneously for making contact.

In one special embodiment of the present invention, the first and second contact elements are inserted into the base element of the housing and fixed by the housing guide element inserted in and interlocked into the base element. The contact elements are then covered and secured against unintentional contact. The base element, by preference, forms the second clamp jaw of the second contact element in one piece. The shockproof arrangement of contact zones or other electrically conductive areas of the contact elements occurs, in particular in all openings of the housing of the device. If necessary the maximum opening of the openings and the clamp jaws are selected such that the electrically conductive parts of the device cannot be touched by human extremities.

Other objects, advantages and salient features of the present invention will become apparent from the following detailed description, which, taken in conjunction with the annexed drawings, discloses preferred embodiments of the present invention.

BRIEF DESCRIPTION OF THE DRAWINGS

Referring to the drawings which form a part of this disclosure.

DETAILED DESCRIPTION OF THE INVENTION

Figure 1:
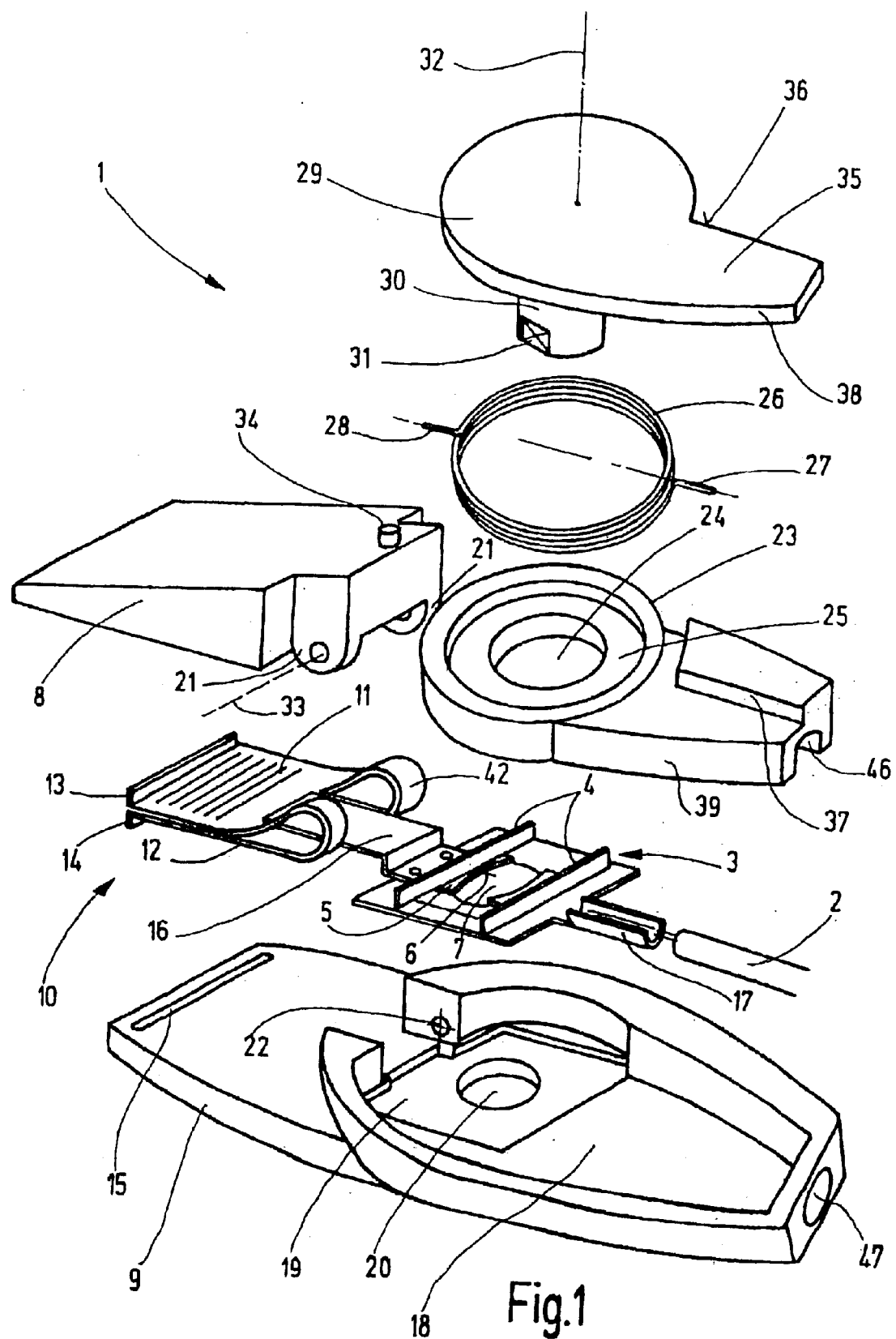
FIG. 1 is an exploded, perspective view of a device according to a first embodiment of the present invention.

FIG. 1 shows the individual parts of the device according to an embodiment of the present invention. The device 1 electrically connects a power lead 2 to an electrode 44, 45 (FIG. 3) and has a first contact element 3 for plugging into a contact stud 43 (FIG. 3) of the electrode 44.

The first contact element 3 is made essentially as disclosed in DE 37 19 474 A1. In particular, the first contact element 3 has two first energy-storing elements 4 extending parallel to one another in their undeflected state. Elements 4 form spring legs providing one contact tongue 5 in one piece each in their middle areas. With their ends spaced apart from the first energy-storing elements 4, the contact tongues 5 form a curved contact zone 6 projecting into a through opening 7. Opening 7 is formed by the first contact element 3 for the contact studs 43 of the electrode 44 to which contact is to be made. The first energy-storing elements 4 are fixed near their long-side ends on the essentially flat first contact element 3.

The device 1 also has a second contact element 10 having two clamp jaws 8 and 9. The contact zones of the second contact element 10 are made in one piece as two elastically deflectable legs 11 and 12 produced in one piece as a punched/bent part from a sheet metal board. The first contact leg 11 is fixed on the first clamp jaw 8, and is preferably inserted into the first clamp jaw 8 by means of the end section 13. End section 13 is bent at a right angle, resulting in clamping. Similarly, the second contact leg 12 is inserted with the end-side section 14 into a receiving slot 15 of the second clamp jaw 9.

The two contact legs 11 and 12 are connected to one another via a connecting section bent into a U-shape. A second energy-storing element 42 of the connecting section provides for spring-loaded contact-making or biasing of the two contact legs 11 and 12 on the film element 45 with which contact is to be made. Furthermore, the two contact legs 11 and 12, in one piece, form a terminal lug 16, by means of which the sheet metal can be fixed on the first contact element 3, especially by a spot-welded. The two contact legs 11 and 12 have ridges, beads or the like corresponding to one another and extending obliquely and especially transversely to the insertion direction of the film electrode 45 with which contact is to be made. At a given clamping force, the film electrode 45 is prevented from being pulled out and the device is to be prevented from falling off the film electrode 45 by the ridges, beads or the like.

On its edge opposite the connection to the two contact legs 11, 12, the first contact element 3 forms a terminal shoe 17 on which the stripped end of the power lead 2 can be fixed, for example by soldering or crimping.

The first contact element 3 is inserted together with the two contact legs 11, 12 into a base element 18 of the housing 1. A recess 19 in base element 18 conforms to the contour of the first contact element 3 and accordingly fixes the first contact element 3. A through opening 20 receives the contact stud 43 of the electrode 44 to which contact is to be made. Through opening 20 is concentric with the through opening 7 of the first contact element 3, and preferably having a somewhat smaller diameter than the latter.

The first clamp jaw 8 forms, in one piece, on its end away from the film electrode 45 with which contact is to be made, two bearing eyes 21. The bearing eyes are spaced axially apart and have one through opening each for the second axis 33. The second axis is supported on the end side in corresponding axial holes 22 in the base element 18.

The guide element 23 is inserted essentially by interlocking into a receiver made in one piece by the base element 18. Thus, the first contact element 3 and the contact legs 11 and 12 are fixed and covered in the base element 18 by guide element 23. Preferably, the guide element 23 is received in base element 18 with its upper surface flush with the upper surface of base element 18, except for the stop surface 37. The guide element has a groove-like guide channel 46 which is flush or axially aligned with a through opening 47 in the base element 18 for clamping the power lead 2 in the housing of the device. This clamping of the power lead provides strain or tension relief for the connection between the power lead 2 and the first contact element 3.

In the area for the first contact element 3, the guide element 23 has a stepped hole, having a round through hole 24 and a staggered transition to an annular shoulder 25 with a larger diameter. A leg or torsional spring 26 can be inserted into the shoulder 25. The spring first end first end 27 can be fixed on the guide element 23. The second end 28 of the leg spring 26 is fixed on the actuating element 29 which can be turned or rotated relative to the guide element 23 against the action of the leg spring 26 acting as the third energy-storing element.

On its surface facing or adjacent the guide element 23, the actuating element 29 has an axle journal 30 which is essentially round in transverse cross section in the portion near the upper flat part of the actuating element 29. The axle journal transverse cross-sectional diameter corresponds to the through hole 24 in the guide element 23 and pivotally supports the actuating element 29 in the guide element 23. On its end away or remote from the flat section of the actuating element 29, the axle journal 30 has an eccentrically extending outside peripheral surface 31 which contacts the first energy-storing element 4 of the first contact element 3 when the actuating element 29 turns. Peripheral surface 31 deforms element 4 such that the contact zones 6 are actuated or moved in the direction away from one another to clear the through opening 7 for the entry of the contact stud 45 of the electrode 44 with which contact is to be made.

At the same time, when the actuating element 29 is being turned about the first axis 32, a guide pin 34 is moved. Guide pin 34 is received with a crank recess on the bottom (not visible in FIG. 1) of the top part of the actuating element 29, with a crank path having a radial component relative to the first axis 32. In this way, as a result of the rotary motion of the actuating element 29 around the first axis 32, rotary motion of the first clamp jaw 8 around the second axis 33 also occurs. Consequently, by turning the actuating element 29, both the first contact element 3 is transferred into the open state, and the second contact element 10, formed by the clamp jaws 8 and 9 together with the contact legs 11 and 12, is opened.

The actuating element 29 in one piece forms an actuating lug 35 with a first edge 36. In the course of rotary motion, first edge 36 comes into contact with the stop surface 37, formed in one piece by the guide element 23, to stop the opening motion of the first and second contact elements 3 and 10. In this position the second edge 38, opposite the first edge 36, for ergonomic reason ends essentially flush with the associated and essentially cylindrical peripheral surface 39 of the guide element 23.

Figure 2:
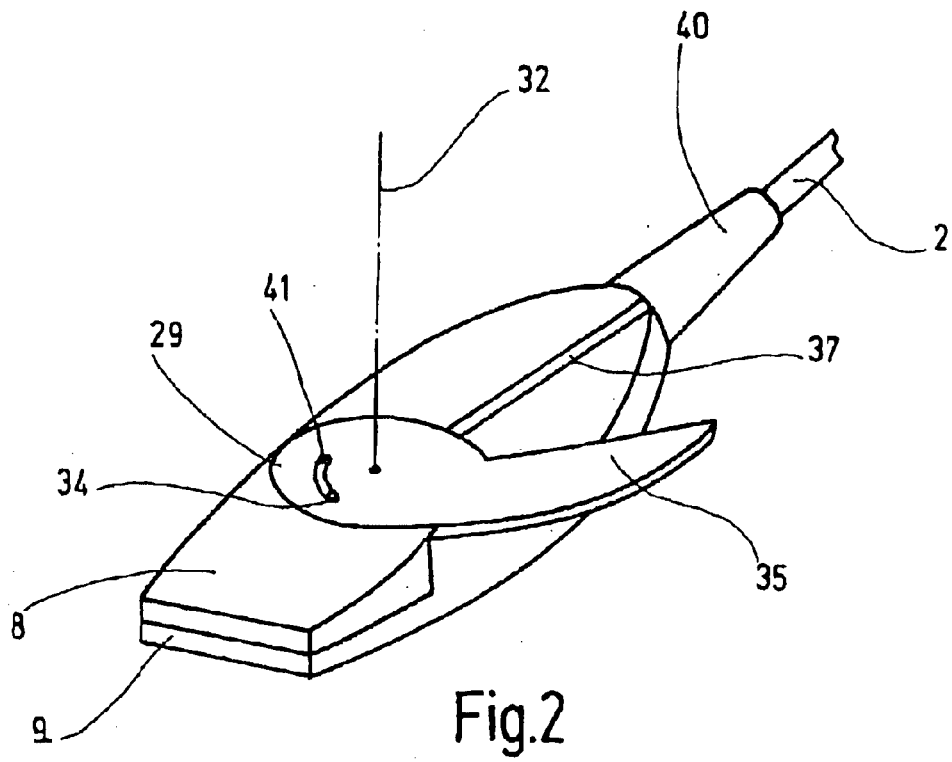
FIG. 2 is a perspective view of a device according to a second embodiment of the present invention.

FIG. 2 shows a perspective view of a second embodiment of the device 1 in the closed position of the two contact elements 3 and 10. Relative to the embodiment of FIG. 1, only the contour at the end of the device 1 facing the power lead 2, and accordingly also the shape of the actuating element 29, are changed slightly. Moreover, in the area of this end, a connecting sleeve 40 is pushed onto the power lead 2 to increase antikink protection. Furthermore, in FIG. 2 the crank 41 is made as a lengthwise through hole into which the guide pin 34 located on the second clamp jaw 8 fits. The radially outside end of the crank 41 also provides a stop for the illustrated position of the actuating element 29 alternatively or in addition to the closed state of the clamp jaws 8 and 9 of the second contact element 10.

Figure 3:
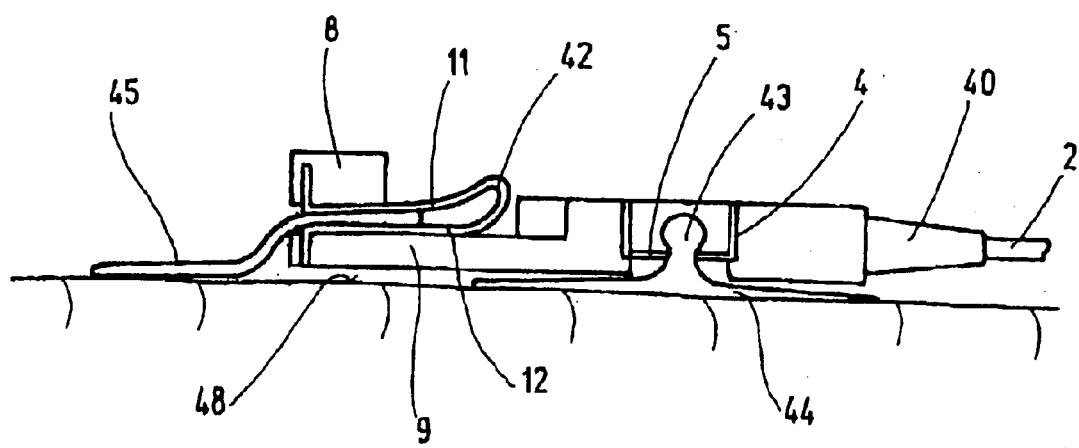
FIG. 3 is a partial, side elevational view in section of the device making contact with the electrodes according to either embodiment of the present invention.

FIG. 3 shows a partial view of a cross section through the device 1 according to the present invention making contact with both the first electrode 44 having a contact stud 43, and a second electrode 45 which is a film electrode. The two electrodes are applied to the surface 48 of the skin, from which physiological data or the corresponding electrical signals are picked up.

While various embodiments have been chosen to illustrate the invention, it will be understood by those skilled in the art that various changes and modifications can be made therein without departing from the scope of the invention as defined in the appended claims.

What is claimed is:

1. A device for electrically connecting a power lead to an electrode, comprising:
   a first contact element for receiving a contact stud of a first electrode, said first contact element having a first spring element biasing a contact zone of said first contact element into an engaging position with the contact stud of the first electrode;
   a second contact element, coupled to said first contact element, having first and second clamping jaws to engage a second electrode therebetween, said jaws being biased by an energy storage toward a closed position; and
   an actuating element pivotable about a first axis and coupled to said second contact element to actuate said jaws to an open position against biasing of said energy storage, said actuating element being coupled to said first contact element to actuate said contact zone of said first contact element to an open position against the biasing of said spring element when said jaws are actuated to said open position thereof.

2. A device according to claim 1 wherein said actuating element comprises a first actuator to deflect said spring element when said actuating element pivots, thereby actuating said contact zone of said first contact element to an open position thereof.

3. A device according to claim 1 wherein a housing receives said contact elements, and includes a guide element; and said actuating element comprises an axle journal pivotally supported in said guide element, one section of said axle journal having an eccentrically extending outside peripheral surface.

4. A device according to claim 1 wherein said actuating element comprises a second actuator that pivots said clamping jaw relative to said second clamping jaw about a second axis against biasing of said energy storage to said open position thereof.

5. A device according to claim 4 wherein said first axis is substantially perpendicular to said second axis.

6. A device according to claim 4 wherein said second actuator comprises a crank guide extending along a crank path having a radial component relative to said first axis.

7. A device according to claim 6 wherein said first clamping jaw comprises a guide pin received in said crank guide to move along said crank path as said actuating element pivots about said first axis.

8. A device according to claim 1 wherein said energy storage comprises a second spring element biasing said second contact element to contact the second electrode.

9. A device according to claim 8 wherein said second contact is formed as one unitary piece of sheet metal and comprises first and second elastically deflectable legs fixed on said first and second clamping jaws, respectively.

10. A device according to claim 1 wherein said first and second contact elements are unitarily formed as one piece.

11. A device according to claim 1 wherein said first and second contact elements are electrically connected.

12. A device according to claim 1 wherein a housing comprises an insulated base element and an insulated guide element receiving said first and second contact elements therebetween, said base and guide elements being connected together and surrounding said contact elements.

13. A device according to claim 12 wherein said base element comprises a portion forming said second clamping jaw as a continuous, unitary part of said base element.

14. A device for electrically connecting a power lead to an electrode, comprising:
a first contact element for receiving a contact stud of a first electrode, said first contact element having a first spring element biasing a contact zone of said first contact element into an engaging position with the contact stud of the first electrode;
a second contact element, coupled to said first contact element, having first and second clamping jaws to engage a second electrode therebetween, said jaws being biased by an energy storage toward a closed position; and
an actuating element pivotable about a first axis and coupled to said second contact element to actuate said jaws to an open position against biasing of said energy storage, said actuating element including a first actuator to deflect said spring element when said actuating element pivots, thereby actuating said contact zone of said first contact element to an open position thereof.

15. A device according to claim 14 wherein a housing receives said contact elements, and includes a guide element; and said actuating element comprises an axle journal pivotally supported in said guide element, one section of said axle journal having an eccentrically extending outside peripheral surface.

16. A device according to claim 14 wherein said actuating element comprises a second actuator that pivots said clamping jaw relative to said second clamping jaw about a second axis against biasing of said energy storage to said open position thereof.

17. A device according to claim 16 wherein said first axis is substantially perpendicular to said second axis.

18. A device according to claim 16 wherein said second actuator comprises a crank guide extending along a crank path having a radial component relative to said first axis.

19. A device according to claim 18 wherein said first clamping jaw comprises a guide pin received in said crank guide to move along said crank path as said actuating element pivots about said first axis.

20. A device according to claim 14 wherein said energy storage comprises a second spring element biasing said second contact element to contact the second electrode.

21. A device according to claim 20 wherein said second contact is formed as one unitary piece of sheet metal and comprises first and second elastically deflectable legs fixed on said first and second clamping jaws, respectively.

22. A device according to claim 14 wherein said first and second contact elements are unitarily formed as one piece.

23. A device according to claim 14 wherein said first and second contact elements are electrically connected.

24. A device according to claim 14 wherein a housing comprises an insulated base element and an insulated guide element receiving said first and second contact elements therebetween, said base and guide elements being connected together and surrounding said contact elements.

25. A device according to claim 24 wherein said base element comprises a portion forming said second clamping jaw as a continuous, unitary part of said base element.

26. A device for electrically connecting a power lead to an electrode, comprising:
a first contact element for receiving a contact stud of a first electrode, said first contact element having a first spring element biasing a contact zone of said first contact element into an engaging position with the contact stud of the first electrode;

a second contact element, coupled to said first contact element, having first and second clamping jaws to engage a second electrode therebetween, said jaws being biased by an energy storage toward a closed position; and an actuating element pivotable about a first axis and coupled to said second contact element to actuate said jaws to an open position against biasing of said energy storage, said actuating element including a second actuator that pivots said clamping jaw relative to said second clamping jaw about a second axis against biasing of said energy storage to said open position thereof, said first axis being substantially perpendicular to said second axis.

27. A device according to claim 26 wherein a housing receives said contact elements, and includes a guide element; and said actuating element comprises an axle journal pivotally supported in said guide element, one section of said axle journal having an eccentrically extending outside peripheral surface.

28. A device according to claim 26 wherein said second actuator comprises a crank guide extending along a crank path having a radial component relative to said first axis.

29. A device according to claim 28 wherein said first clamping jaw comprises a guide pin received in said crank guide to move along said crank path as said actuating element pivots about said first axis.

30. A device according to claim 26 wherein said energy storage comprises a second spring element biasing said second contact element to contact the second electrode.

31. A device according to claim 30 wherein said second contact is formed as one unitary piece of sheet metal and comprises first and second elastically deflectable legs fixed on said first and second clamping jaws, respectively.

32. A device according to claim 26 wherein said first and second contact elements are unitarily formed as one piece.

33. A device according to claim 26 wherein said first and second contact elements are electrically connected.

34. A device according to claim 26 wherein a housing comprises an insulated base element and an insulated guide element receiving said first and second contact elements therebetween, said base and guide elements being connected together and surrounding said contact elements.

35. A device according to claim 34 wherein said base element comprises a portion forming said second clamping jaw as a continuous, unitary part of said base element.

36. A device for electrically connecting a power lead to an electrode, comprising:

a first contact element for receiving a contact stud of a first electrode, said first contact element having a first spring element biasing a contact zone of said first contact element into an engaging position with the contact stud of the first electrode;

a second contact element, coupled to said first contact element, having first and second clamping jaws to engage a second electrode therebetween, said jaws being biased by an energy storage toward a closed position; and an actuating element pivotable about a first axis and coupled to said second contact element to actuate said jaws to an open position against biasing of said energy storage, said actuating element including a second actuator that pivots said clamping jaw relative to said second clamping jaw about a second axis against biasing of said energy storage to said open position thereof, said second actuator having a crank guide extending along a crank path having a radial component relative to said first axis.

37. A device according to claim 36 wherein a housing receives said contact elements, and includes a guide element; and said actuating element comprises an axle journal pivotally supported in said guide element, one section of said axle journal having an eccentrically extending outside peripheral surface.

38. A device according to claim 36 wherein said first clamping jaw comprises a guide pin received in said crank guide to move along said crank path as said actuating element pivots about said first axis.

39. A device according to claim 36 wherein said energy storage comprises a second spring element biasing said second contact element to contact the second electrode.

40. A device according to claim 39 wherein said second contact is formed as one unitary piece of sheet metal and comprises first and second elastically deflectable legs fixed on said first and second clamping jaws, respectively.

41. A device according to claim 36 wherein said first and second contact elements are unitarily formed as one piece.

42. A device according to claim 36 wherein said first and second contact elements are electrically connected.

43. A device according to claim 36 wherein a housing comprises an insulated base element and an insulated guide element receiving said first and second contact elements therebetween, said base and guide elements being connected together and surrounding said contact elements.

44. A device according to claim 43 wherein said base element comprises a portion forming said second clamping jaw as a continuous, unitary part of said base element.

45. A device for electrically connecting a power lead to an electrode, comprising:

a first contact element for receiving a contact stud of a first electrode, said first contact element having a first spring element biasing a contact zone of said first contact element into an engaging position with the contact stud of the first electrode;

a second contact element, coupled to said first contact element, having first and second clamping jaws to engage a second electrode therebetween, said jaws being biased by an energy storage toward a closed position;

an actuating element pivotable about a first axis and coupled to said second contact element to actuate said jaws to an open position against biasing of said energy storage; and a housing having an insulated base element and an insulated guide element receiving said first and second contact elements therebetween, said base and guide elements being connected together and surrounding said contact elements, said base element including a portion forming said second clamping jaw as a continuous, unitary part of said base element.

46. A device according to claim 45 wherein said actuating element comprises an axle journal pivotally supported in said guide element, one section of said axle journal having an eccentrically extending outside peripheral surface.

47. A device according to claim 45 wherein said actuating element comprises a second actuator that pivots said clamping jaw relative to said second clamping jaw about a second axis against biasing of said energy storage to said open position thereof.

48. A device according to claim 47 wherein said first axis is substantially perpendicular to said second axis.

49. A device according to claim 47 wherein said second actuator comprises a crank guide extending along a crank path having a radial component relative to said first axis.

50. A device according to claim 49 wherein said first clamping jaw comprises a guide pin received in said crank guide to move along said crank path as said actuating element pivots about said first axis.

51. A device according to claim 45 wherein said energy storage comprises a second spring element biasing said second contact element to contact the second electrode.

52. A device according to claim 51 wherein said second contact is formed as one unitary piece of sheet metal and comprises first and second elastically deflectable legs fixed on said first and second clamping jaws, respectively.

53. A device according to claim 45 wherein said first and second contact elements are unitarily formed as one piece.

54. A device according to claim 45 wherein said first and second contact elements are electrically connected.

* * * * *